(12) United States Patent
Smollar

(10) Patent No.: US 9,788,780 B2
(45) Date of Patent: Oct. 17, 2017

(54) ALLERGY SKIN TEST APPLICATOR, AND RELATED TESTING TRAY, TESTING KIT AND TESTING METHOD

(71) Applicant: Marvin Smollar, Delray Beach, FL (US)

(72) Inventor: Marvin Smollar, Delray Beach, FL (US)

(*) Notice: Subject to any disclaimer, the term of this patent is extended or adjusted under 35 U.S.C. 154(b) by 94 days.

(21) Appl. No.: 14/329,253

(22) Filed: Jul. 11, 2014

(65) Prior Publication Data

US 2015/0289794 A1 Oct. 15, 2015

Related U.S. Application Data

(60) Provisional application No. 61/978,379, filed on Apr. 11, 2014.

(51) Int. Cl.
| | |
|---|---|
| *A61B 5/00* | (2006.01) |
| *A61B 50/22* | (2016.01) |
| *A61B 50/20* | (2016.01) |
| *A61B 50/30* | (2016.01) |
| *A61B 50/33* | (2016.01) |
| *A61B 90/94* | (2016.01) |
| *A61B 10/00* | (2006.01) |
| *A61B 50/00* | (2016.01) |

(52) U.S. Cl.
CPC .............. *A61B 5/411* (2013.01); *A61B 5/441* (2013.01); *A61B 10/0035* (2013.01); *A61B 50/20* (2016.02); *A61B 50/22* (2016.02); *A61B 50/30* (2016.02); *A61B 50/33* (2016.02); *A61B 90/94* (2016.02); *A61B 2010/0003* (2013.01); *A61B 2050/006* (2016.02); *A61B 2050/0067* (2016.02)

(58) Field of Classification Search
CPC .... A61B 17/205; A61B 10/0035; A61B 5/411
USPC .......................................................... 600/556
See application file for complete search history.

(56) References Cited

U.S. PATENT DOCUMENTS

| | | | | |
|---|---|---|---|---|
| 3,556,080 | A | * | 1/1971 | Hein .................... A61B 17/205 600/556 |
| D247,822 | S | * | 5/1978 | Hein ............................ 600/556 |
| 4,237,906 | A | * | 12/1980 | Havstad ............... A61B 17/205 215/250 |
| 4,711,247 | A | * | 12/1987 | Fishman .............. A61B 17/205 600/556 |
| 5,396,989 | A | | 3/1995 | Hein |
| 5,647,371 | A | | 7/1997 | White, Jr. et al. |

(Continued)

*Primary Examiner* — Daniel Cerioni
(74) *Attorney, Agent, or Firm* — Laurence A. Greenberg; Werner H. Stemer; Ralph E. Locher

(57) ABSTRACT

An allergy testing kit contains a plurality of allergy testing applicators, an allergy testing tray and a plurality of allergen bottles each containing an allergen. Each of the applicators contains an elongated handle, a plurality of arms extending from the elongated handle and disposed in an asymmetrical configuration, and a plurality of legs with tines extending from each of the arms. The allergy testing tray contains a main body having an underside and a top surface, a cover for locking with the main body and a plurality of reservoirs extending from the underside of the main body. The reservoirs each have a chamber with an opening extending from the top surface. The reservoirs are disposed in different groups and each group has an asymmetrical configuration matching that of the applicator.

9 Claims, 17 Drawing Sheets

(56) References Cited

U.S. PATENT DOCUMENTS

| | | | | |
|---|---|---|---|---|
| 5,673,705 | A | * | 10/1997 | Pitesky ............... A61B 17/205 600/556 |
| 5,738,108 | A | | 4/1998 | Hein |
| 5,792,071 | A | | 8/1998 | Hein |
| 5,871,452 | A | * | 2/1999 | Baker .................... A61B 5/441 600/556 |
| 6,322,520 | B1 | * | 11/2001 | Baik ........................ A61B 5/00 600/556 |
| 6,554,777 | B1 | | 4/2003 | Hein, Jr. |
| D629,518 | S | | 12/2010 | Hein, Jr. et al. |
| 7,922,672 | B2 | | 4/2011 | Hein, Jr. et al. |
| 8,469,900 | B2 | | 6/2013 | Hein, Jr. et al. |
| 8,491,909 | B2 | | 7/2013 | Esch |
| 2006/0167375 | A1 | * | 7/2006 | Terrassse ............... A61B 5/411 600/556 |
| 2010/0022910 | A1 | * | 1/2010 | Lane .................... A61B 5/0059 600/556 |
| 2013/0138013 | A1 | * | 5/2013 | Hein, Jr. ................ A61B 5/411 600/556 |

\* cited by examiner

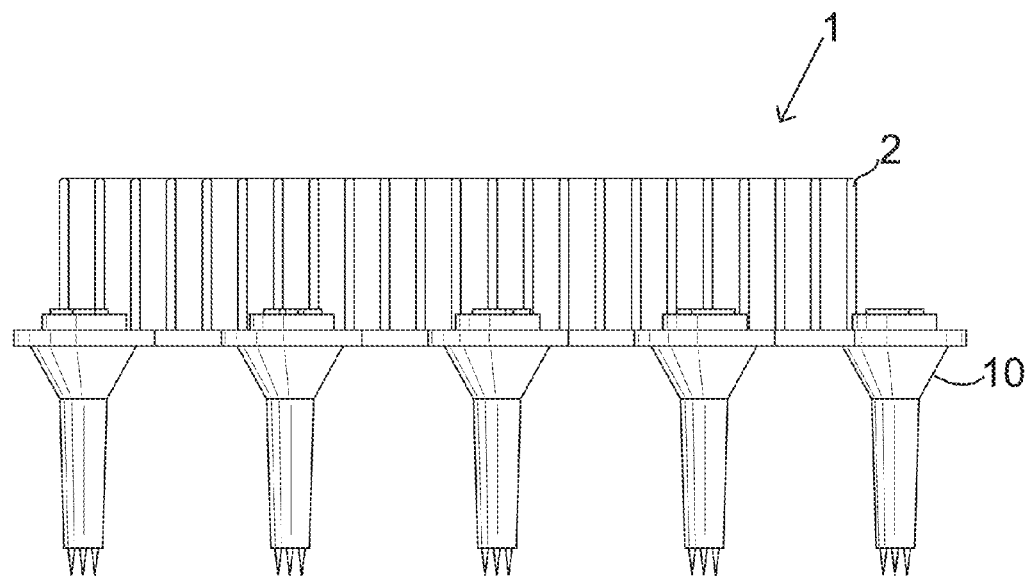
FIG. 4
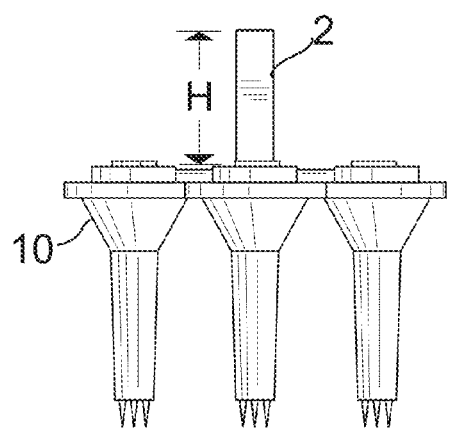 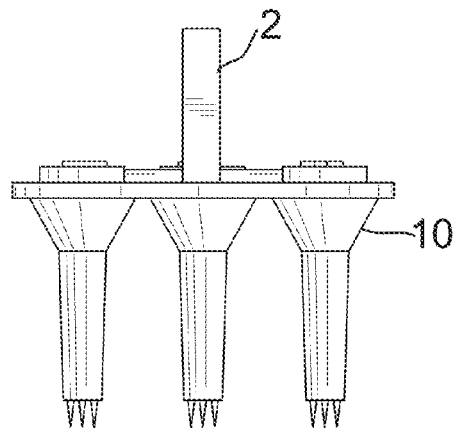
FIG. 5    FIG. 6

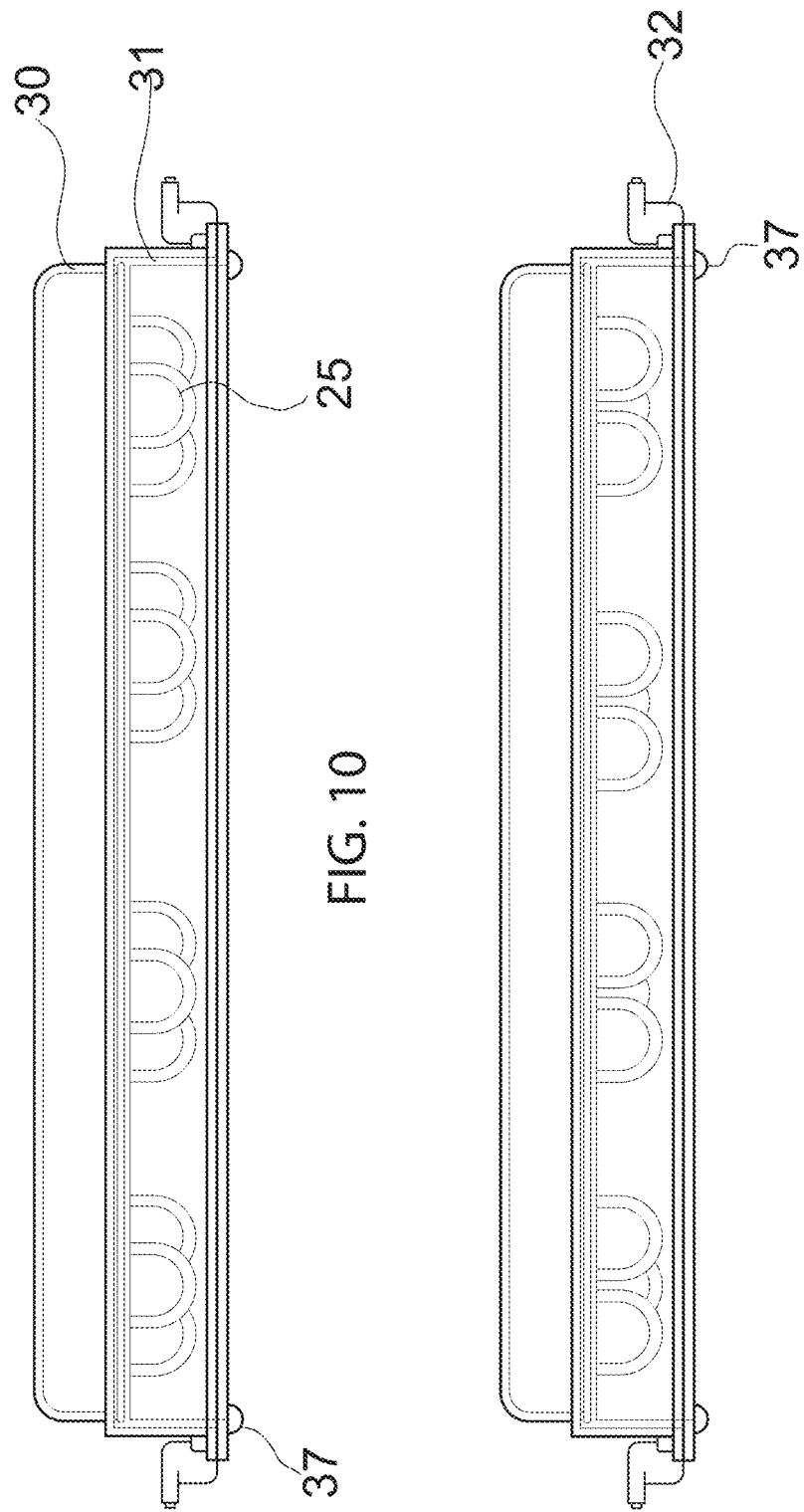

A — Foods

| Site | Allergens | (mm) |
|---|---|---|
| A1 | Positive control | |
| A2 | Negative control | |
| A3 | Cow's Milk | |
| A4 | Whole Eggs | |
| A5 | Tomato | |
| A6 | Fish Mix | |
| A7 | Strawberry | |
| A8 | Soybean | |
| A9 | Whole Wheat | |

B — Pollens & Grasses

| Site | Allergens | (mm) |
|---|---|---|
| B1 | Nettle Pollen | |
| B2 | Pecan Pollen | |
| B3 | Maple Pollen | |
| B4 | Bahia Grass | |
| B5 | Bermuda Grass | |
| B6 | Johnson Grass | |
| B7 | Timothy Grass | |
| B8 | Perennial Ryegrass | |
| B9 | June Grass | |

C — Grass & Weeds

| Site | Allergens | (mm) |
|---|---|---|
| C1 | Cocklebur | |
| C2 | English Plantain | |
| C3 | Kochia | |
| C4 | Lambs Quarters | |
| C5 | Rough Marsh Elder | |
| C6 | Careless Weed | |
| C7 | Tall Ragweed | |
| C8 | Short Ragweed | |
| C9 | Rough Pigweed | |

D

| Site | Allergens | (mm) |
|---|---|---|
| D1 | Russian Thistle | |
| D2 | Sheep Sorrel | |
| D3 | Western Water Hemp | |
| D4 | Cotton Linters | |
| D5 | Mugwort | |
| D6 | Sagebrush | |
| D7 | Rhodotorula | |
| D8 | Sacc. Cerevisiae | |
| D9 | Grain Smut Mix | |

E — Molds

| Site | Allergens | (mm) |
|---|---|---|
| E1 | Candida Albicans | |
| E2 | Acremonium | |
| E3 | Drechslera | |
| E4 | Curvularia | |
| E5 | Trichophyton | |
| E6 | Fusarium | |
| E7 | Mixed Penicillium | |
| E8 | Aspergillus | |
| E9 | Alternaria | |

F — Trees

| Site | Allergens | (mm) |
|---|---|---|
| F1 | Australian Pine | |
| F2 | Eucalyptus | |
| F3 | Melaleuca | |
| F4 | Olive, Russian | |
| F5 | Elm American | |
| F6 | Sycamore, American | |
| F7 | Red Birch | |
| F8 | Red Mulberry | |
| F9 | Cedar, Red | |

G — Trees 2

| Site | Allergens | (mm) |
|---|---|---|
| G1 | Shagbark Hickory | |
| G2 | Alder | |
| G3 | White Ash | |
| G4 | White Oak | |
| G5 | Virginia Live Oak | |
| G6 | California Live Oak | |
| G7 | Cottonwood | |
| G8 | Box Elder | |
| G9 | Bald Cypress | |

H

| Site | Allergens | (mm) |
|---|---|---|
| H1 | Queen Palm | |
| H2 | Feather Mix | |
| H3 | Horse Hair | |
| H4 | Cat Hair | |
| H5 | Cattle Hair | |
| H6 | Dog Hair | |
| H7 | American Cockroach | |
| H8 | Mite Pteronyssinus | |
| H9 | Mite Farinae | |

FIG. 19

ALLERGY SKIN TEST APPLICATOR, AND RELATED TESTING TRAY, TESTING KIT AND TESTING METHOD

CROSS-REFERENCE TO RELATED APPLICATION

This application claims the priority, under 35 U.S.C. §119, of U.S. provisional patent application No. 61/978,379, filed Apr. 11, 2014; the prior application is herewith incorporated by reference in its entirety.

BACKGROUND OF THE INVENTION

Field of the Invention

An allergy skin testing kit and a testing method are configured to simplify the allergy skin testing process so that it may be routinely employed by a none allergy specialist, such as a family medicine physician, dermatologist, pediatrician and the like. There is a growing population of allergic disease sufferers and therefore a growing need to address these medical issues, as well as reduce the cost attributable to specialists being required to manage this population. This scenario of modern chronic disease management is not unfamiliar to general practitioners as exampled by the need for the general practitioner to manage their vast population of type II diabetes sufferers outside of the specialist endocrinologist office. By enabling the general practitioners, for example, to perform routine allergy skin testing in their own office to confirm their diagnosis and direct specific treatment, the patient's medical issues can be more readily addressed and the cost of identifying and medically treating this widespread problem can be greatly reduced.

U.S. Pat. Nos. 5,738,108 and 6,554,777 to Hein (hereinafter Hein) teach prior art testing apparatuses containing a testing applicator and a testing tray. The testing applicator can be easily mishandled as the small applicator body is hard to grip and there is no bottom finger support. The test applicator is built symmetrical with a hard to see numbering system, contributing to the possibility of error in the event the testing applicator is placed in reverse position in the testing tray or on the patient's skin, thereby resulting in false readings. Furthermore, there is no form fit between the legs of the testing applicator and the open wells of the testing tray allowing for the evaporation of the allergenic material contained in the reservoirs. In addition, the testing trays are not covered in a sealed fashion which means the allergens can be more easily exposed to contamination and evaporation or accidental mishandling by the medical personnel.

Therefore, there is a need for an improved apparatus where it is impossible to place the testing applicator improperly in the testing tray and which has a clearly visible numbering system thereby significantly reducing the possibility of errors in reading the test results. In addition the applicator needs to be configured to provide a more secure grip that also improves the uniform application of pressure through the testing device to the patient's skin, as well as reducing the evaporation of the allergenic material. Furthermore the allergy testing tray needs to be configured to assist in reducing evaporation of the allergen and provide for secure handling over multiple tests.

SUMMARY OF THE INVENTION

The simplification and usefulness of the invention comes, in part, from including a broad range of allergenic agents in premeasured, easy to empty containers, arrayed and labeled in a simple, logical pattern, such as an alpha-numeric arrangement, for example, as opposed to scientific names, thereby facilitating a more predictable and consistent application by those in a more general medical setting. The test kit provides a broad spectrum of pre-selected allergenic agents, derived from leading authorities, including foods, molds, pollens, grasses, trees, fungus and animal and insect related allergens, among others. The pre-determined selection provides the pediatrician or general practitioner, e.g., with the intrinsic knowledge of the appropriate allergenic materials to employ without having to organize and source their own panel of allergens, which would typically require considerable time dealing with scientific literature and with unfamiliar botanical and biological descriptions; such a time commitment is a significant barrier to the non-specialist adoption of allergy skin testing. The simple logic pattern used for the labeling and organizing of the allergens and concomitant reporting system enables the delegation of the filling process and even the testing procedure to more junior staff under the supervision of a physician. Since testing for allergies often requires testing for a large number of allergies, often 36 or 72, the premeasured containers, whose contents are completely emptied at the initial set up of the test kit, and provide sufficient allergenic material for a pre-determined, multiple number of tests, substantially eliminates the amount of time needed to organize and prepare the test apparatus for the testing of each allergy patient. It is a result of the original design of the apparatus that set up time for a multiplicity of tests is so greatly reduced. In a busy general practitioner's office this time saving feature has considerable benefit.

In an example of a preferred embodiment, the allergen containers are arrayed in a preloaded vacuum tray in a pattern that matches the alignment of the reservoir openings on the test case, as well as the test reports. The pattern is coded, for example, A through H, to match a similar preferred embodiment of the identifiers displayed on the surface of the test case and throughout the test reporting system.

The ability to provide for a multiplicity of tests with only one initial set up is made feasible by the unique features of the allergy test case, which contains a multiplicity of reservoirs for holding the allergenic material and its secure handling and sealing features. The reservoirs are arranged in an asymmetrical pattern that coincides directly with the coding of the premeasured filling system and the asymmetry of the test applicators. The use of a simple, predetermined coding system for identifying what is consistently placed in each reservoir avoids the arduous process of labeling each reservoir for each test and likewise reduces the potential for errors by reducing potential variability.

The test case configuration also incorporates a secure sealing of the allergenic material by providing an elastic air seal in locking engagement between the top and bottom halves of the test case. The locking engagement is created by a releasable latch mechanism that brings a downwardly projecting flange located in the test case cover into a compressive relation with the elastic seal located in the bottom of the case. Creating a sealed and locked enclosure not only reduces evaporation of the allergenic materials, it also provides for more secure handling, thereby avoiding spillage or slippage of components or other forms of accidents. In the preferred embodiment the sealing of the reservoirs is further enhanced by shaping the top of the reservoirs parabolically so as to mate in a sealing engagement with the parabolic end of the applicators that are also part of the test kit. When the case is locked, the top of the case exerts a small downward pressure on any applicators situated in the reservoirs, thereby creating an effective closure of the reservoir, further reducing evaporation and spillage. The amount of pressure is controlled by the degree of engagement between the elastic air seal and the downward engaging means situated inside the case cover. Because the test kit is configured for a multiplicity of tests, the secure handling of the test apparatus becomes very important. The handling and stability of the test case is further enhanced by creating a space between the bottom of the case and the resting surface on which the case is placed by adding raised, non-slip feet at the bottom of each corner making the lifting of the case from a flat surface more secure and convenient, while also reducing the likelihood of accidental slippage, that might otherwise have knocked the test case off the resting surface had it not been for the non-slip feet inclusion in the invention.

The test kit also provides a prepackaged number of asymmetrical skin test applicators. Each applicator is configured to complement the asymmetrical alignment of the test case reservoirs. The tips of the applicators are configured to perform percutaneous skin scratch testing. The benefit of the asymmetrical arrangement of test reservoirs and matching asymmetrical applicators is a substantial departure from the prior art and is a major step in reducing, if not, avoiding errors in the reading of test results. The applicator has leg like extensions that extend between the skin testing tip and the upper structure of the applicator. The upper portion of each leg of the applicator is configured to mate in a sealing engagement with the top of the reservoir openings in the test case. In a preferred embodiment the shape of the upper portion of each leg matches the shape of the reservoir opening so as to form a sealing engagement when in contact. The asymmetry of the applicator legs and tips contains a minimum number of three legs and tips. The use of an applicator with an asymmetrical arrangement of testing tips is a significant factor in reducing human error in the administration of the test by registering a clear record of the test sites even if the applicator is mistakenly reversed in direction when applied to the skin. The number of applicators in each kit is calculated to match the premeasured amount of allergenic material, thereby providing the convenience of coordinated test supplies at the ready for a multiple number of tests.

The applicator tips are configured to utilize capillary action so as to receive a limited and consistent amount of allergenic material from the contents of the reservoir. The applicator design provides a significant improvement in the usability and the consistency of the test results by adding horizontally extending shoulders with upwardly projecting outer edges along with strengthened arms that hold each applicator leg and tip. The shoulder extensions and the juxtaposed terminus edges provide a significant enhancement for controlling the applicator while also enabling a more effective means to apply uniform downward pressure, as compared to the prior art embodiments. The strengthening of the arm extensions on each applicator also adds to the applicator's ability to deliver uniform pressure. Uniform pressure across all applicator tips is essential for reliable test results.

The test kit also includes a test report, individually packaged for each pre-determined number of tests in the kit. The test report is pre-coded to match the coded allergenic array in the test case reservoirs, which likewise match the arrangement of the coded, premeasured containers holding the allergenic materials. By adhering to the common code throughout, observing and reporting the results follows a consistent pattern, test after test, thereby making it easier for the non-specialist to read and report the test results.

In addition to the coded test report, the test kit comes complete with all the paper work required for performing and recording the patient's test results, pre-packaged in individual units for each patient's test. The paper work includes authorization from the patient, a gauge for measuring the results of any wheal and flare clinical allergic reaction, as well as literature regarding the test procedure for the patient to read while waiting for the test results. By providing the paperwork in prepackaged, individual units, so as to have a complete set organized and ready for each patient in advance, simplifies the administration of the testing procedure while also lessening the potential for not having a complete paper file on the patient. This is especially important for the physician's office whose frequency of administering such tests may be less frequent than that of an allergy specialist and thereby lessening the omission of misplaced essential forms.

Some of the realizable advantages of the herein disclosed allergy test kit and test method are that the test kit and method can: 1. Provide the general medical practitioner with a comprehensive allergy skin testing apparatus in a convenient, unitary design; 2. The design of the test case makes for easier handling while significantly reducing the potential for spillage and evaporation of the very costly allergen fluids by providing both a sealing and releasable locking mechanism for the test case; 3. Greatly reduces the confusion and possibility of error during the administration of the allergy skin scratch test by use of an asymmetrical, multiple tip test applicator, thereby registering a clear record of the test sites even if the applicator is mistakenly applied in an inverted (reverse) order to the skin; 4. The applicator's asymmetry also avoids having an applicator placed into the allergen filled wells in reverse order, thereby reducing potential error when reading the skin test reactions incorrectly; 5. An applicator design that increases the leverage and control over the delivery of the allergen material to the patient's skin and thereby providing for a more reliable percutaneous delivery of the allergen material; 6. Reduce the complexity and fragility of the testing equipment while enhancing the storability of the apparatus; 7. Simplify the filling of the allergens into the test wells by providing pre-measured quantities of the allergen materials specific to the number of patients to be tested per kit, typically a multiplicity of tests; 8. Reducing technician error by use of a simple and uniformly coordinated coding system, such as, an alphabetical-numeric coding vs. scientific names, for all of the relevant test elements, including: the pre-measured allergen containers, the test case reservoirs and the parallel test report; 9. Significantly reduce doctor or technician time needed to fill the test reservoirs by using an easy to dispense container that contains a premeasured quantity of the allergen material that is sufficient in quantity to provide for the number of multiple patients to be tested per kit and that is fully emptied at the initial test set up; 10. Enhance the stability and handling of the test case by creating a space between the bottom of the case and the resting surface on which the case is placed by the use of a raised, non-slip feet placed on each corner of the bottom of the case; and 11. Provide a simplified method of recording test results that avoid error because of the use of coordinated grading report that is aligned in parallel with the test case reservoir openings.

With the foregoing and other objects in view there is provided, in accordance with the invention, an allergy testing applicator. The applicator includes an elongated handle, a plurality of arms extending from the elongated handle and having an asymmetrical configuration, and a plurality of legs having tines extending from each of the arms.

In accordance with an added feature of the invention, the number of the arms and the legs is an odd number.

In accordance with another feature of the invention, the elongated handle has a first end and a second end, and one of the arms extends directly from one of the first or second ends.

In accordance with an addition feature of the invention, a shoulder extends transversely from both long sides of the elongated handle. Ideally, the shoulders extend out ⅛-¼ inches from the elongated handle.

In accordance with a further feature of the invention, the handle has a bottom side and the shoulders extend out from the bottom side of the handle.

In accordance with yet another feature of the invention, the legs have a main body region and an upper tapered region extending from the main body region and being wider than the main body region. Ideally, the upper tapered region is conical or parabolic in shape.

In accordance with a further added feature of the invention, there are provided raised indicators, and one of the raised indicators is disposed on a top side of each of the arms.

In accordance with another additional feature of the invention, the elongated handle has a plurality of ribs formed at right angles thereon for assisting a hand of a user to grip the elongated handle.

In accordance with a concomitant feature of the invention, there are provided reinforcements extending along a top of the arms.

With the foregoing and other objects in view there is provided, in accordance with the invention, an allergy testing tray. The allergy testing tray has a main body with an underside and a top surface and a plurality of reservoirs extending from the underside of the main body. The reservoirs each having a chamber formed therein with an opening extending from the top surface into the chamber. The reservoirs are disposed in different groups each having an asymmetrical configuration. A removable cover is provided which locks to the main body.

In accordance with an added feature of the invention, the groups of the reservoirs contain an odd number of reservoirs. Ideally, there are eight of the groups of the reservoirs extending from the main body. However, any number of groups is possible (e.g. 1, 2, 3, 4, 5, 6, 7, 8, 9, 10, 11, 12, etc.).

In accordance with an additional feature of the invention, a seal is disposed in the main body and the cover has a flange engaging the seal when the cover is secured to the main body.

In accordance with a further feature of the invention, the openings of the reservoirs have a smaller cross-section than the chambers of the reservoirs.

In accordance with another feature of the invention, the main body has flanges and the cover has latches for engaging the flanges and locking the cover to the main body.

In accordance with another added feature of the invention, the openings are tapered openings.

In accordance with yet another feature of the invention, non-slip feet are disposed on a bottom of the main body.

In accordance with a concomitant feature of the invention, the reservoirs are color coded.

With the foregoing and other objects in view there is provided, in accordance with the invention an allergy testing kit containing a plurality of allergy testing applicators. Each applicator contains an elongated handle, a plurality of arms extending from the elongated handle and disposed in an asymmetrical configuration, and a plurality of legs with tines extending from each of the arms. The test kit further has an allergy testing tray having a main body with an underside and a top surface, a cover for locking with the main body, and a plurality of reservoirs extending from the underside of the main body. The reservoirs each have a chamber formed therein with an opening extending from the top surface. The reservoirs are disposed in different groups each having an asymmetrical configuration matching the asymmetrical configuration of the applicator. The test kit additionally has a plurality of allergen bottles each containing an allergen.

In accordance with an added feature of the invention, the allergen bottles, the applicators and the reservoirs are grouped and coded for quick identification of belonging to which group.

Other features which are considered as characteristic for the invention are set forth in the appended claims.

Although the invention is illustrated and described herein as embodied in an allergy applicator, a testing tray, a testing kit and testing method, it is nevertheless, not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 4 is a side view of the allergy testing applicator;

FIG. 5 is a rear view of the allergy testing applicator;

FIG. 6 is a front view of the allergy testing applicator;

FIG. 10 is a front view of the allergy testing tray;

FIG. 11 is a rear view of the allergy testing tray;

FIG. 19 is an illustration of a data sheet showing color and alpha-numeric coordination of the allergens.

DETAILED DESCRIPTION OF THE INVENTION

Figure 1:
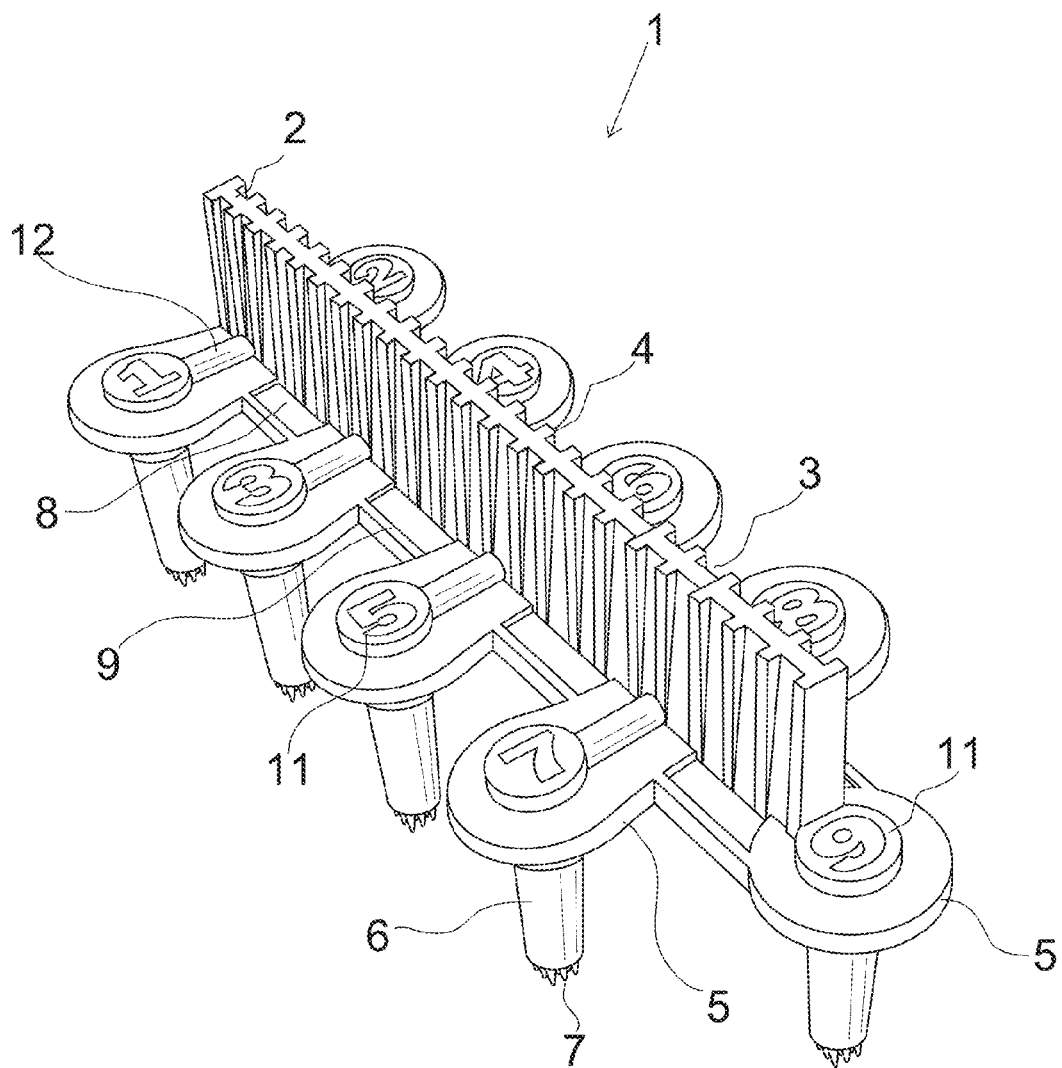
FIG. 1 is a diagrammatic, side perspective view of a first embodiment of an allergy testing applicator according to the invention.
Figure 2:
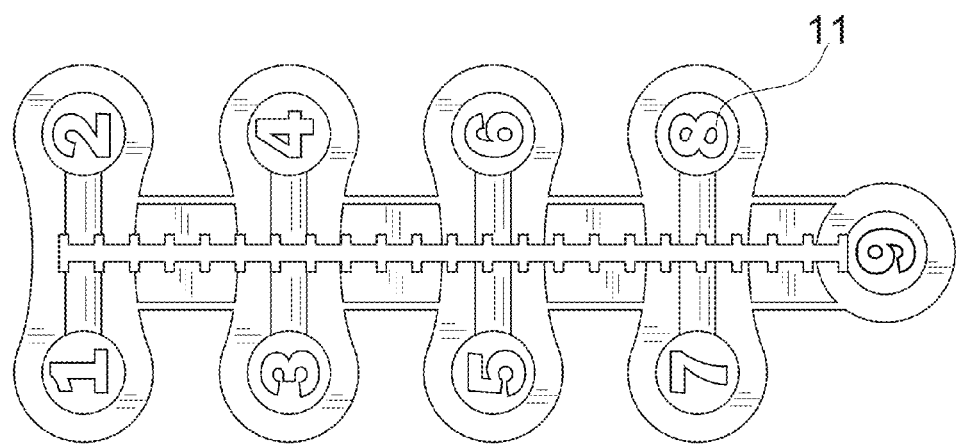
FIG. 2 is a top plan view of the allergy testing applicator.
Figure 3:
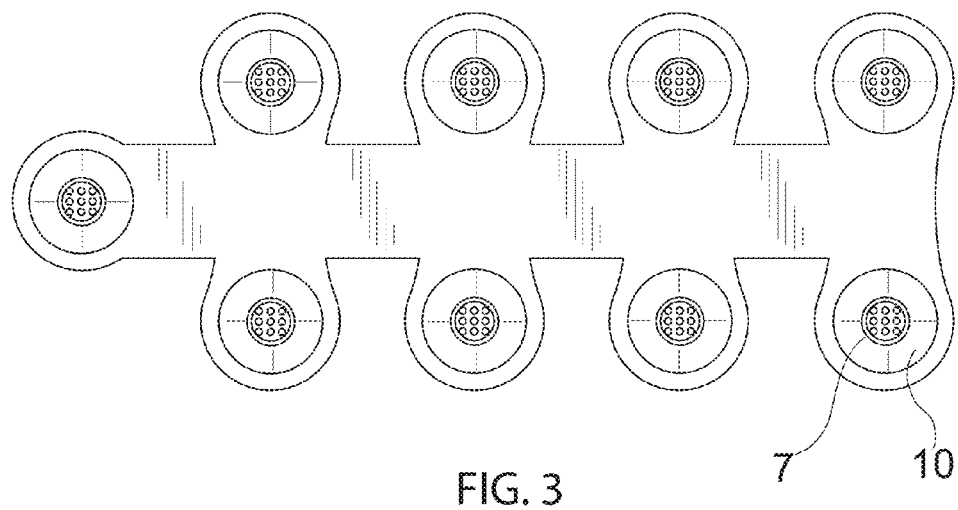
FIG. 3 is a bottom plan view of the allergy testing applicator.

Referring now to the figures of the drawings in detail and first, particularly to FIGS. 1-6 thereof, there is shown an applicator 1 having a handle 2 that spans nearly an entire length of the applicator 1 and forms a rigid structural spine. The handle 2 has relatively deep grooves 3 and ribs 4 across its entire length, cut at 90 degrees to the handle 2, so as to provide a good engaging surface that will enhance a user's grip, especially for users wearing protective gloves. The handle 2 has a height H of 9/16" but can be in a range of 7/16"-13/16" ideally (see FIG. 5). A plurality of arms 5 extend outwardly from the handle 2. The arms 5 are disposed in an asymmetric configuration around the handle 2. Leg like structures 6 extend downwardly from each of the arms 5. At a lower end of each leg 6 is a multiplicity of finely formed tines 7 that constitute the portion of the applicator 1 that engages with a patient's skin. The arrangement and shape of the tines 7 provide a means for holding a specific amount of allergenic material that is then transferred to an area of contact on the patient's skin via a forward and backward, side-to-side rocking motion of the applicator 1 on the patient (e.g. back or arm). The transfer of the allergenic material from the tines 7 to the patient's epidermis thereby engages the immune system's reaction to test for allergy sensitivity to the particular allergenic material. The tines 7 have a length of 1-4 mm, ideally 2.5 mm.

The applicator 1 has significant additional features that facilitate the proper testing protocol and transfer of allergenic material to the patient's epidermis. The applicator 1 has horizontally extending shoulders 8 with upwardly projecting outer edges or ridges 9, more specifically the shoulders 8 extend out transversely from the handle 2 between 1/8"-1/4". The shoulder extensions 8 and the juxtaposed terminus edges 9 provide a significant enhancement for controlling the applicator 1 while also enabling more effective means to apply uniform downward pressure while executing the proper testing motion, as compared to the prior art embodiments. In other words, the shoulders 8 provide a surface area for the tips of the finger for helping to apply an even pressure and assisting in executing a rocking motion of the applicator 1. To further deliver a more uniform pressure on a patient's skin, each of the arm extensions 5 has a reinforcement 12. Uniform pressure is essential for reliable test results.

Figure 8:
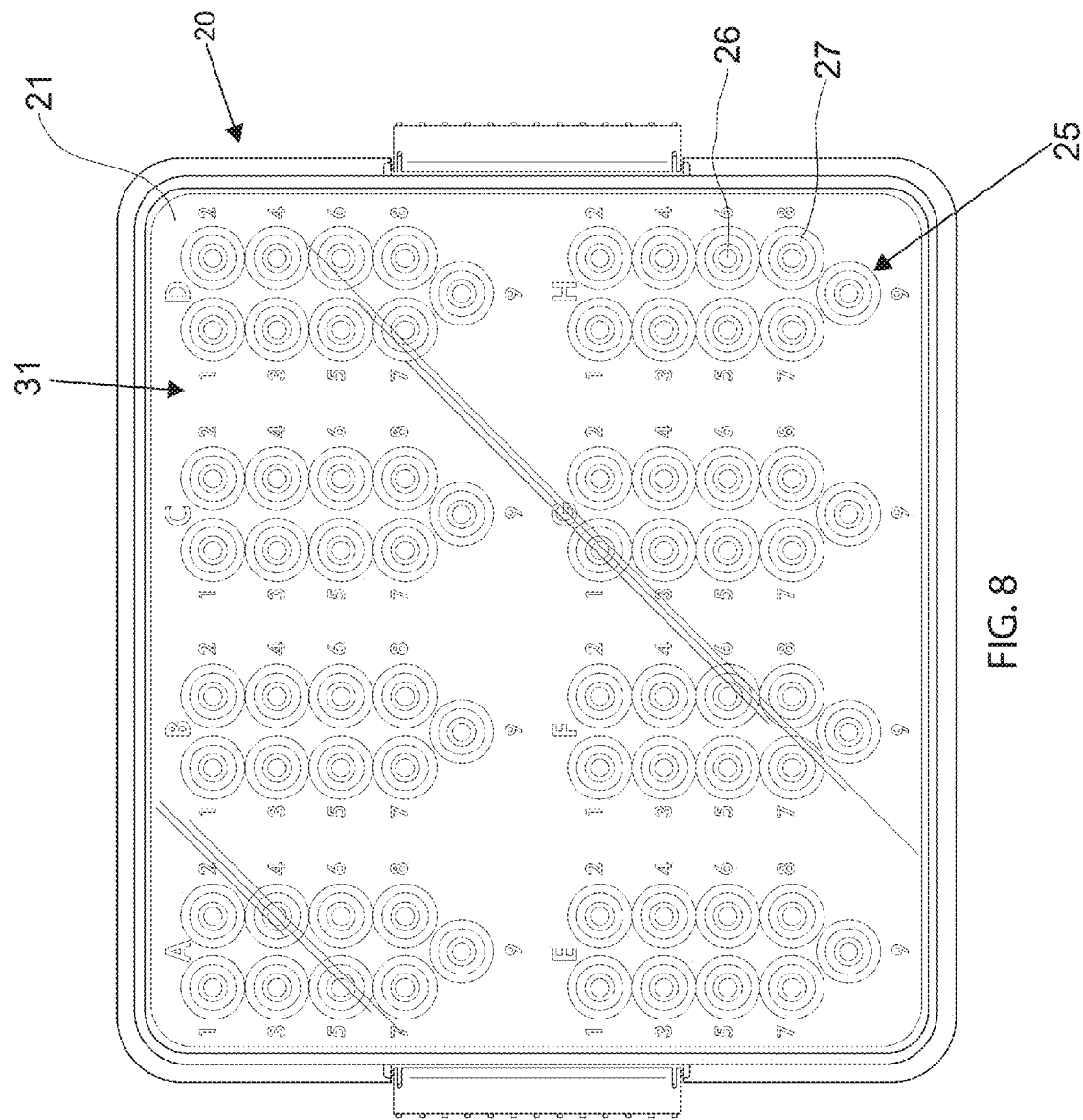
FIG. 8 is a diagrammatic, top plan view of a first embodiment of an allergy testing tray.
Figure 9:
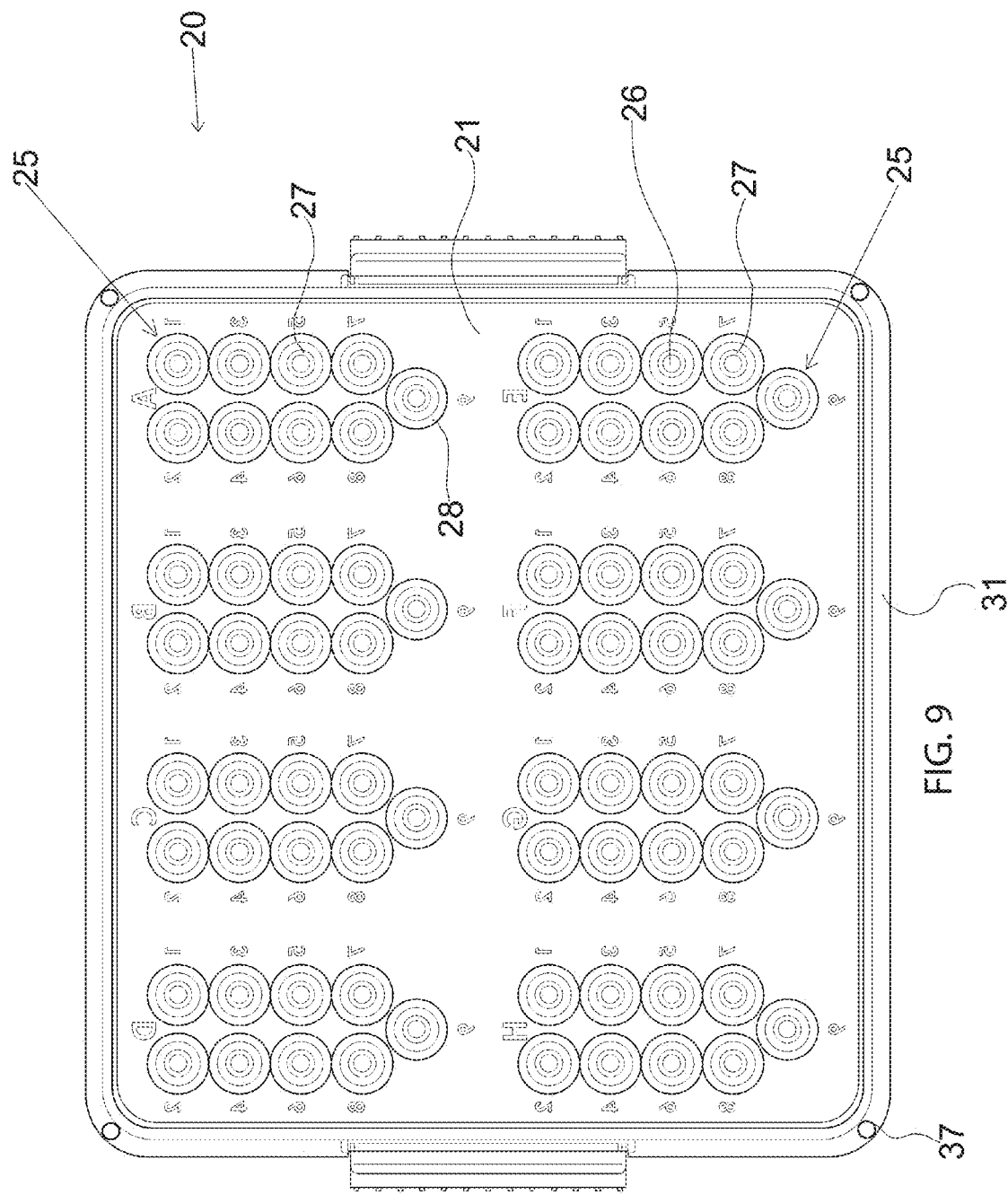
FIG. 9 is a bottom plan view of the allergy testing tray.
Figure 12:
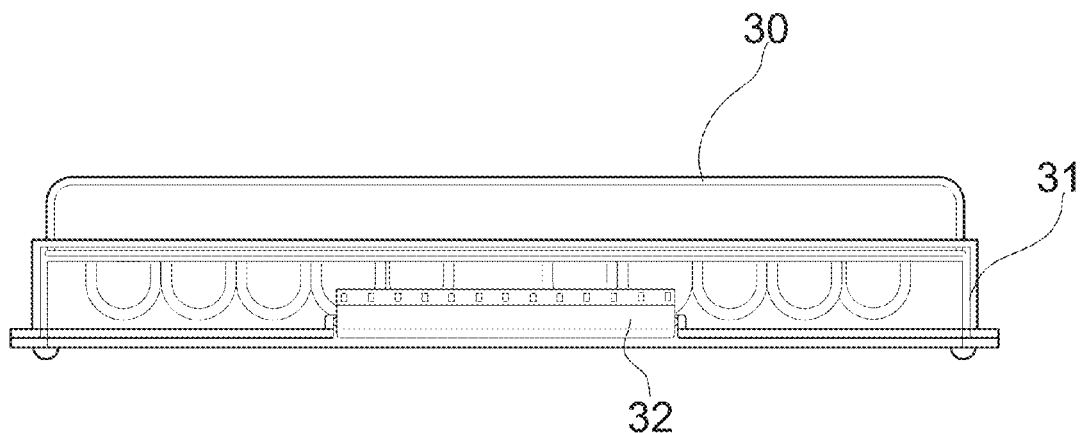
FIG. 12 is a left side view of the allergy testing tray.

The design of a preferred embodiment of the applicator 1 is asymmetrical with nine arms 5 and are arranged to complement the asymmetrical alignment of test case reservoirs 25 (see FIG. 8). The tips 7 of the applicators 1 are configured to perform percutaneous skin scratch testing. The benefit of the asymmetrical arrangement of test reservoirs 25 and matching asymmetrical applicators 1 is a substantial departure from the prior art and is a major step in avoiding errors in the reading of test results. The applicator 1 has the leg like extensions 6 that extend between the skin testing tip 7 and an upper structure 10 of the applicator 1. The upper portion 10 of each leg 6 is configured to mate in a sealing engagement with a top 27 of reservoir openings 26 in a test case 20 (see FIGS. 2, 3, 8 and 13A). In a preferred embodiment, the shape of the upper portion 10 of each leg 6 matches a shape of the reservoir opening 26 so as to form a sealing engagement when in contact (see FIG. 13A). The asymmetry of the applicator legs 6 requires a minimum of three legs. The ideal number of legs can be 3, 5, 7, 9 as shown, 11 and 13 (e.g. an odd number).

The applicator tips 7 are configured to utilize capillary action so as to receive a limited and consistent amount of allergenic material from the contents allergens disposed in the reservoirs 25. The number of tips 7 shown is 9, but can be any number of tips. The applicator 1 configuration provides a significant improvement in the usability and the consistency of the test results by adding the horizontally extending shoulders 8 with the upwardly projecting outer edges 9 along with strengthened arms 5 that hold each applicator leg 6 and associated tips 7.

As shown in FIGS. 1-6, the applicator 1 has a plurality of identifying numbers 11 (1-9, e.g.) that are raised and prominent. In this manner the numbers 11 are easy to read and the user is less likely to make mistakes.

Figure 7:
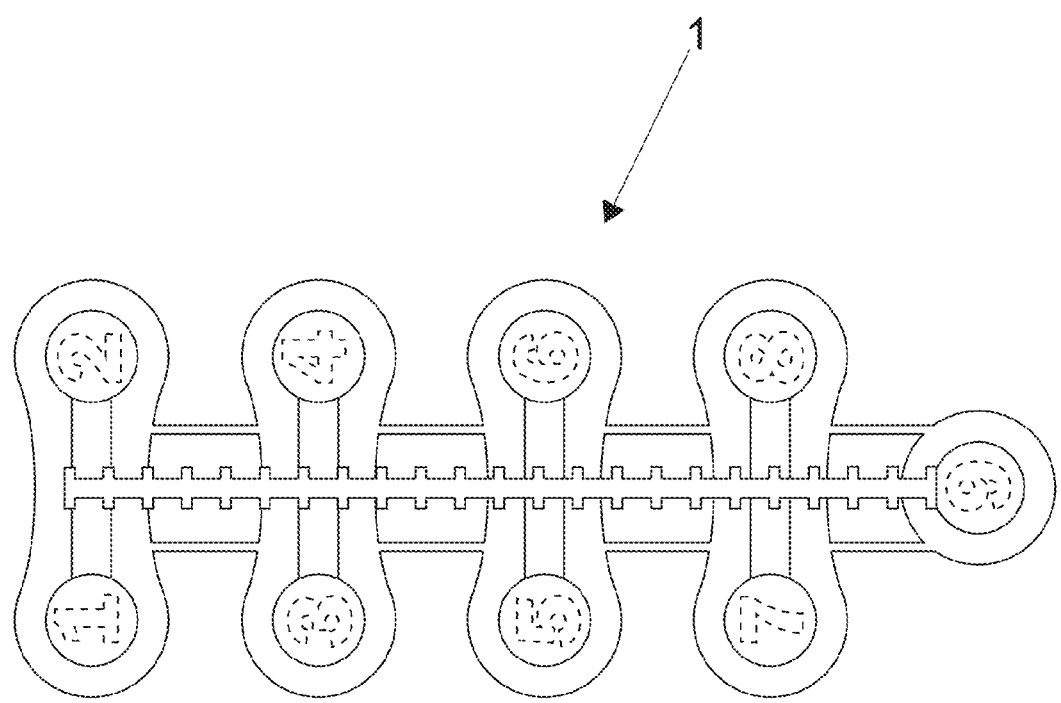
FIG. 7 is a top plan view of a second embodiment of the allergy testing applicator.

FIG. 7 shows a second embodiment of the applicator 1 which has no numbers. Proper orientation and placement are provided by the asymmetry of the applicator 1.

FIGS. 8-16 show an allergy test case or testing tray 20. The allergy test case 20 provides a main body 31 having an applicator engaging surface 21 (see FIGS. 8 and 13A). The applicator engaging surface 21 can include a plurality of test reservoirs 25 (see FIGS. 8-10 & 13A) each having a plurality of applicator engaging openings 26 and configured in an asymmetrical arrangement (e.g. an odd number of reservoirs that are offset). In a preferred embodiment, the applicator engaging openings 26 are defined by a parabolically shaped surface 27 to fittingly engage with a mating surface being the upper leg portion 10 of the applicator 1 so as to provide enhanced sealing and reduction of evaporation and or leakage of the allergens disposed in the reservoirs 25 (see FIG. 13A). Each of the test reservoirs 25 has a chamber 28 for receiving an allergen. The chambers 28 have a diameter or cross-sectional area being greater than the applicator engaging openings 26 (the openings 26 are smaller than the chambers 28). Because the openings 26 are smaller and the openings 26 are sealed by the arms 6, 10 of the applicator 1, evaporation of the costly allergens is greatly reduced during storage. The applicator engaging surface 27 is disposed on the allergen case 20, such that the applicator engaging openings 26 align with the plurality of allergen reservoirs 25. The applicator engaging surface 27 and the reservoirs 25 are integrally formed from the allergen case 20 or permanently attached to the allergen case 20.

As previously described, the reservoirs 25 are identified by a simple code that is uniformly used throughout the system. The preferred embodiment shows an alphanumeric arrangement A1-A9 . . . H1-H9. It coincides with the alphanumeric arrangement of allergen bottles 40 (see FIGS. 17, 18 & 18A). In the preferred embodiment, each of the reservoirs 25 corresponds to a code on the label on each allergen bottle 40 that is delivered with the kit. The allergens, for example, can be delivered in individual bottles/containers 40 that are labeled A1-A9 through H1-H9 such that a user can simply squeeze all the allergenic material into the appropriate reservoir 25. The bottle labeled A-7 would be emptied into a reservoir numbered 7 in pattern A, bottle B-9 would be emptied into a reservoir numbered 9 in pattern B and so on. The user matches coded allergen bottles 40 with the like coded allergen reservoir 25, thereby avoiding the need of labeling and keeping track of Latin, botanical or biological names. In a preferred embodiment the reservoirs 25 and the allergen bottles 40 are all color coded in a coordinating fashion. For example the allergen bottles 40 are colored or labeled with blue and the reservoirs A1-A9 are identified by blue coloring (e.g. a blue marker above the reservoir, the reservoir itself is blue or the numbers A1-A9 are blue). Similarly, another series of allergen bottles 40 are colored or labeled green, and the reservoirs B1-B9 are identified by green coloring, etc. (see FIGS. 17 and 18).

In the preferred embodiment the reservoirs 25 and engaging applicators 1 are arranged in an asymmetrical pattern (the number of reservoirs is odd and the odd reservoir is offset). The asymmetry pattern is significant in that it helps to avoid human error when transferring the applicators 1 from the allergy case 20 to the patient's skin. With a symmetrical pattern common in the trade (e.g. prior art), reversal of top or bottom locations can easily occur if the medical personnel turnaround or rotate the applicators from one end to the other when switching hands, e.g., which can easily lead to mistaken interpretation of test results.

The allergy test case includes a cover 30 configured to releasably engage the main body or lower portion 31 of the allergy case 20 (see FIG. 10). The cover 30 can interface with the lower portion 31 of the allergen case 20 in any number of ways, such as a latch. In the preferred embodiment a pivoted latch 32 (see FIG. 11) is configured to engage with a flange 33 (see FIG. 14) located on a base 34 of the case 20 (see FIG. 14). To improve a sealing quality of the test case, a flexible seal 35 (see FIG. 14A) is positioned along the entire circumference of the lower portion 31 of the test case 20 so that when the cover 30 is locked, the seal 35 engages with a flange 36 that extends downwardly from the cover 30 so as to create a sealing engagement (see also FIGS. 13& 13A). The bottom of the allergy test case has raised, non-slip members or feet 37 for secure placement of the case on a surface.

Figure 13:
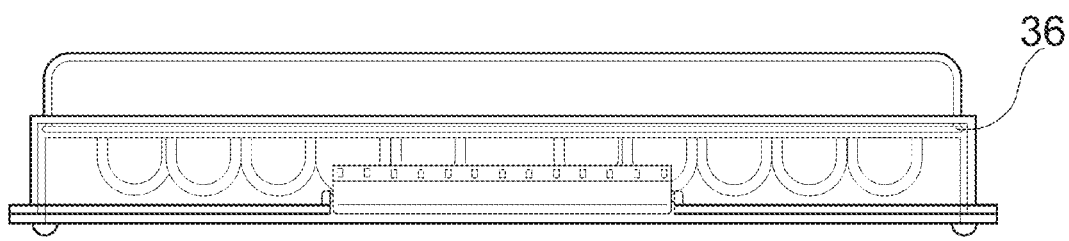
FIG. 13 is a right side view of the allergy testing tray.
Figure 13A:
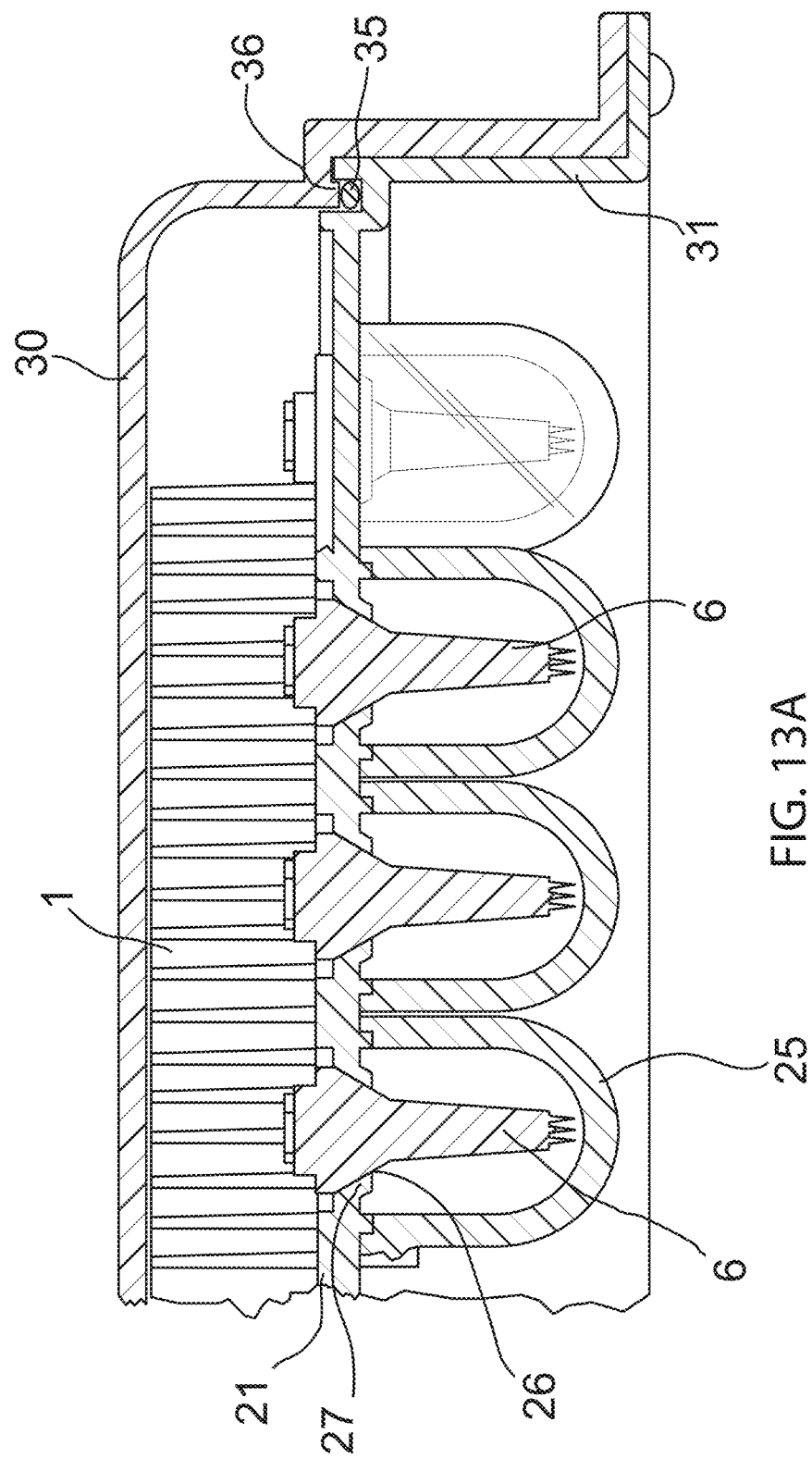
FIG. 13A is a cross-section view of a part of the testing tray and the applicator showing a downward extending flange, a seat for the elastic seal and a sealing engagement between a top of reservoirs and a top of an applicator leg.
Figure 14:
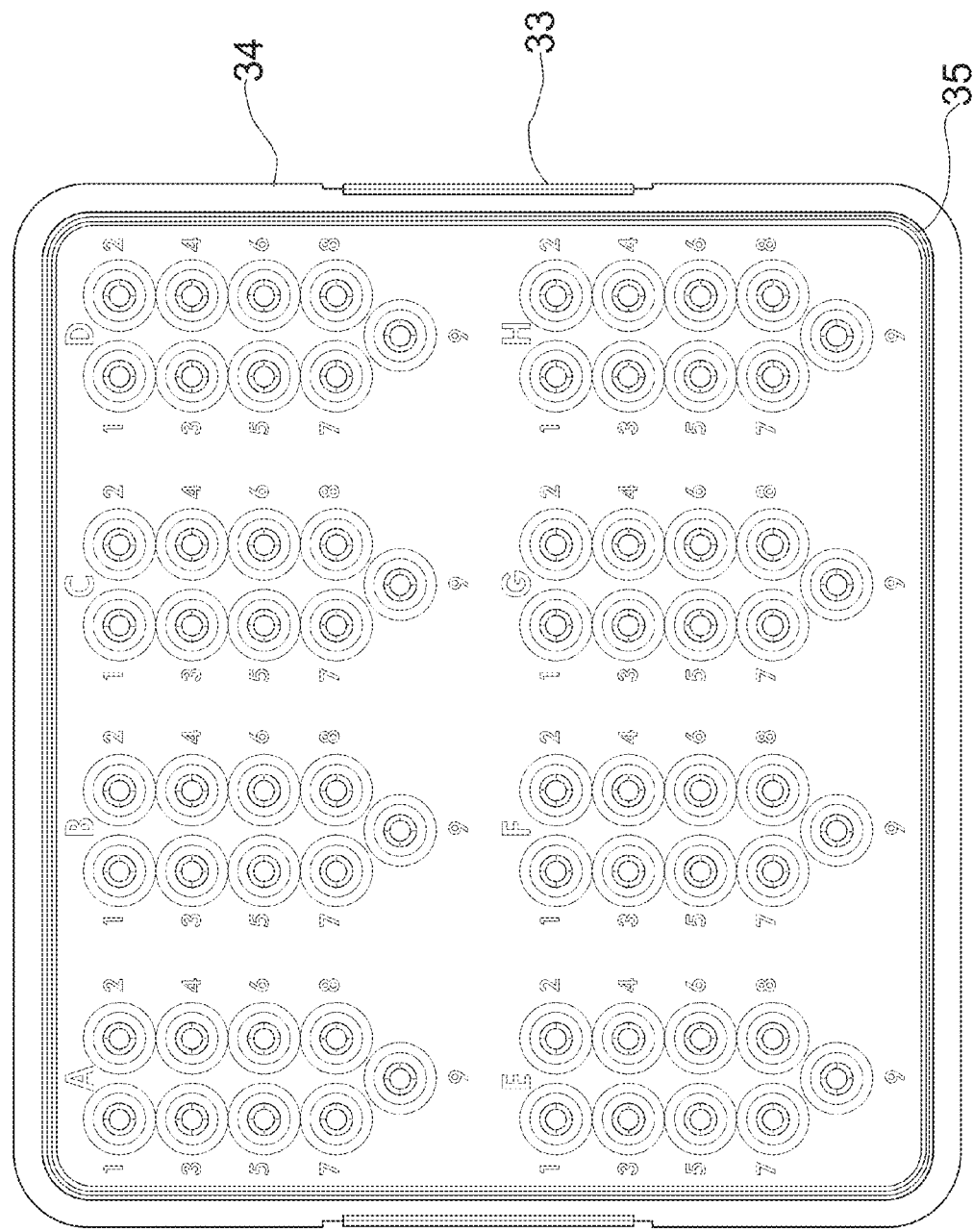
FIG. 14 is a top plan view of the allergy testing tray with the cover removed.
Figure 14A:
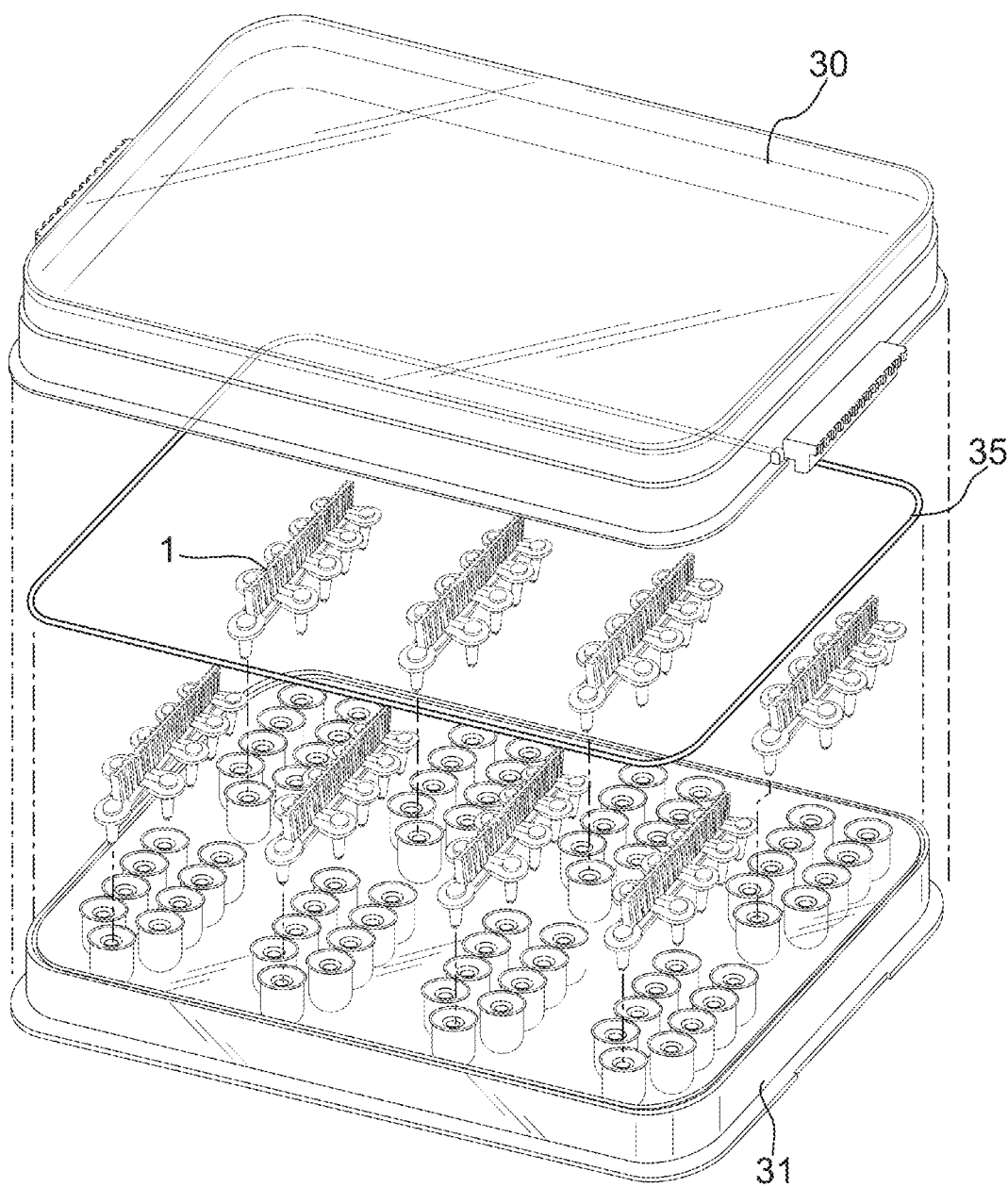
FIG. 14A is an exploded, perspective view of the testing tray showing a configuration of an elastic sealing device that encircles a bottom of the testing tray.
Figure 15:
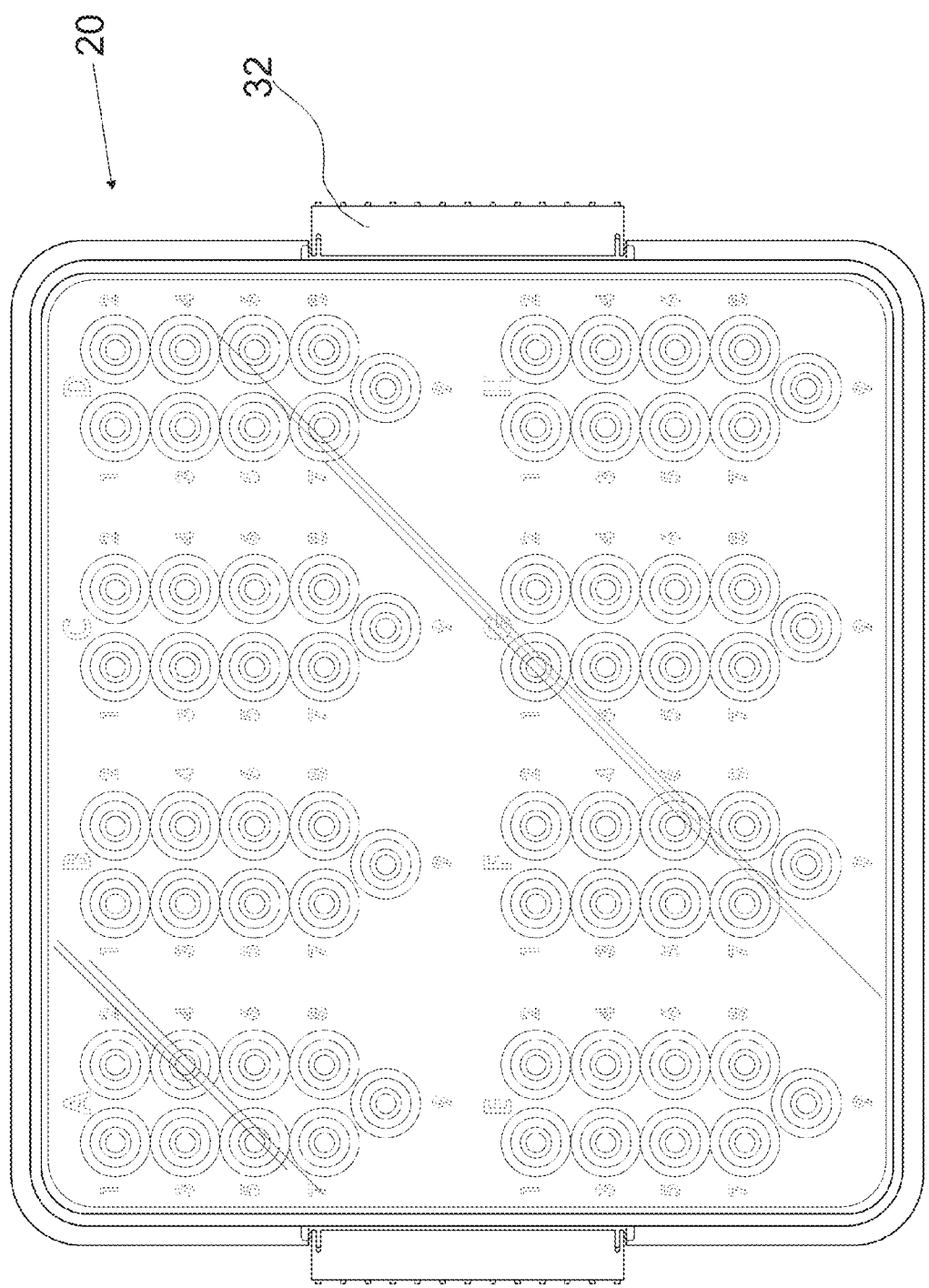
FIG. 15 is a top plan view of a second embodiment of the allergy testing tray where the dashed lines show environmental matter.
Figure 16:
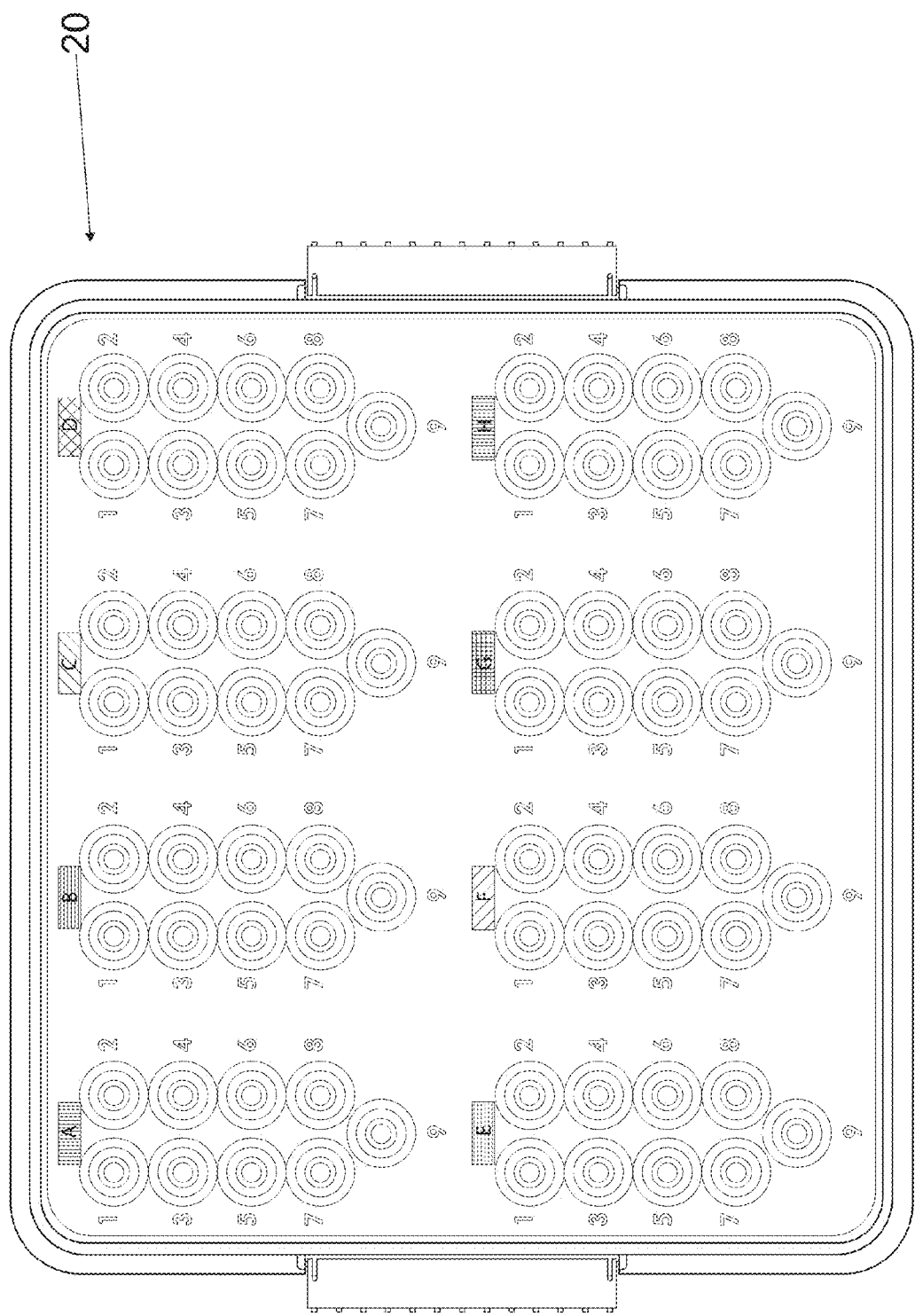
FIG. 16 is a top plan view of a third embodiment of the allergy testing tray where the lettering is disposed in colored rectangular markers, the first and third embodiments being the same except for the colored rectangular markers.

The cover 30 may be dimensioned such that when it is located on top of the main body or lower portion 31 of the case, when applicators 1 are positioned in the reservoirs 25 the cover 30 can interact with the handle portion 2 of the applicators 1 (e.g. inside bottom of the cover presses on the handle portion 2, see FIG. 13A). When the self-contained latching mechanism is engaged so as to gently press the applicators 1 into engagement with the reservoir openings 26, while the cover 30 also engages the elastic seal 35, thereby enhancing the sealing arrangement of the test case 20.

FIG. 13A is a cross-sectional view of a section of the assembled test kit prepped for storage. New applicators 1 are disposed in all of the reservoirs 25. The cover 30 presses on the handle 2 thus pushing the arms 6, 10 into the reservoirs 25 thus making a sealing engagement. Please see how the tapering 27 of the opening 26 engages the corresponding tapering of the upper portion of leg 6. Further note how the flange 36 engages the seal 35 providing a sealed engagement.

Figure 17:
FIGS. 17 and 18 are perspective views of allergens that are contained in individual bottles/containers that are labeled A1-A9 through H1-H9 such that a user can simply squeeze all allergenic material into an appropriate reservoir.
Figure 18:
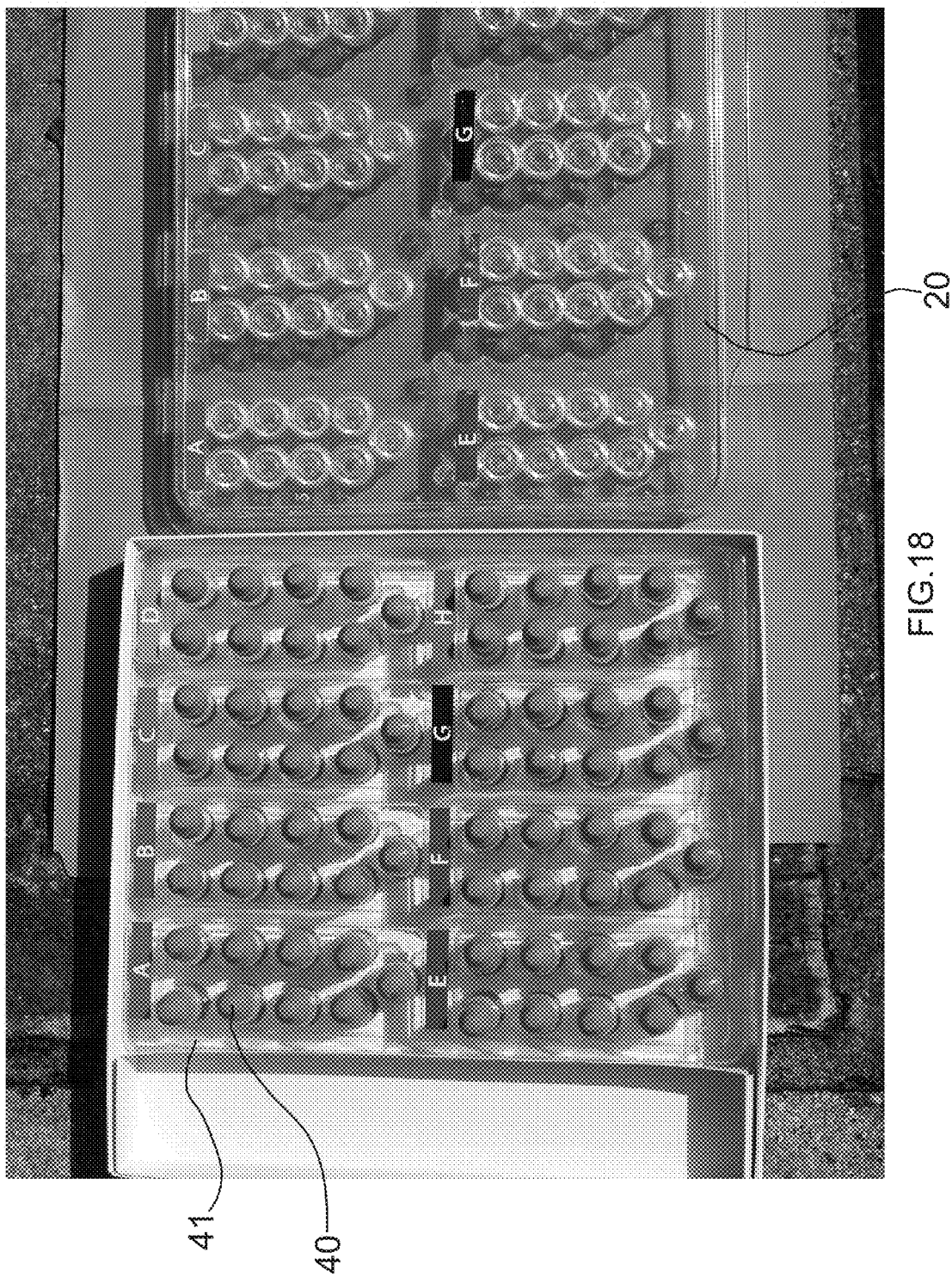

FIGS. 17 and 18 show possible configurations of the allergen containers 40. The allergen containers 40 are held in a holding tray 41 in a matching logical sequence following the coded pattern used throughout the testing system. More specifically, each allergen container 40 has a color coded label 42 containing an alpha-numeric coding matching that of the reservoirs 25. FIG. 18 shows the holding tray 41 next to the allergy testing tray 20 and it is clear to see how easy it is to load the proper allergen bottle 40 in the proper reservoir 25 to the alpha-numeric and/or color coded location.

Figure 18A:
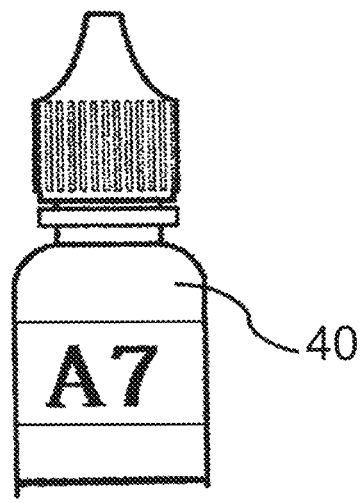
FIG. 18A is a front view showing a coded allergen bottle A-7.

FIG. 18A shows an enlarged view of the allergen bottle 40 relating to the alpha-numeric location A-7.

FIG. 19 shows a test report that is pre-coded (e.g. colored and alpha-numeric) to match the coded allergenic array in the test case reservoirs 25, which likewise match what was in the coded, premeasured containers 40. By adhering to the common code throughout, observing and reporting the results follows a consistent pattern, thereby making it easier and less error prone for the non-specialist to read and report the test results.

The testing method is now described in detail with the following steps.

1. Label a predetermined number of easy to empty containers 40 with a simple coding system (FIG. 19), such as an alphanumeric code. For example, A-1 to A-9, B-2, B-3, H-1 through H-9 or any desired numbering.

2. Pre-fill the predetermined number of containers 40 with a specifically measured amount of allergenic material so as to provide sufficient allergenic material for the number of test the test kit is configured to perform.

3. Arrange all of the filled allergenic containers 40 in a holding tray 41 in a logical sequence following the coded pattern.

4. Seal the holding tray 41 of pre-filled allergenic materials so it may be handled or shipped without disturbing the logical sequence of the containers.

5. At the initiation of the first allergy test, open the sealed holding tray 41 of pre-filled allergenic materials.

6. Remove the cover 30 from the supplied test case 20.

7. Note the coded pattern on the surface of the test case 20, the pattern being coded to match the coding of the prefilled containers holding the allergenic material.

8. Fill the test case reservoirs 25 with the entire contents of the containers 40 of allergenic material, being careful to match the coded sequence so that container 40 numbered A-1 fills reservoir 25 lettered A-1 and container 40 numbered C-3 fills reservoir 25 numbered C-3 and so on in logical order.

9. Insert a matching number of asymmetrical applicators 1 into the reservoir openings 26, thereby loading the allergenic material on the tips 7 of the applicators 1.

10. Using the applicators 1 that have been loaded with allergenic agents via the reservoir, perform the intended multiple sites skin test (e.g. apply each applicator 1 to the skin of the patient).

11. Dispose of each applicator 1 once it is been used to perform the percutaneous skin test.

12. Once all of the predetermined allergens have been properly applied to the patient and the used applicators 1 are disposed of properly, it is preferable that the test case 20 should be reloaded with a new set of sterile applicators 1 that come prepackaged in the kit to match the number of asymmetrical reservoirs and in sufficient number to match the number of tests available from the pre-measured allergenic material.

13. Place the cover 30 of the test case 20 back into position and secure the test case 20 shut using the self-contained locking device 32 so that the case is ready for the next test or to be stored, preferably, in a refrigerated environment.

14. As soon as sufficient time has elapsed for the test to be effective, record the skin wheal and flare reaction results on the pre-printed chart (FIG. 19), provided as part of the test kit, that is arranged to match the coding of the allergen containers and test case reservoirs so that the sequence, for example, A-1 to A-9 through H-1 to H-9, is identical to the test sequence.

The invention claimed is:

1. An allergy skin testing applicator, comprising:
an elongated handle;
a plurality of arms extending from said elongated handle, said plurality of arms having an asymmetrical configuration wherein said arms are disposed on opposite sides of said elongated handle except for an odd numbered arm being disposed on a center line and offset from said arms situated on said opposite sides of said elongated handle; and
a plurality of legs each having tines and a respective one of said legs extending from a respective one of said arms, said respective leg extending from said odd numbered arm having a top and said elongated handle extending a distance into said top of said odd numbered arm, said legs having a main body region and an upper tapered region extending from said main body region and being wider than said main body region, all of said upper tapered region being distal from said tines.

2. The allergy testing applicator according to claim 1, wherein a number of said arms or said legs is an odd number selected from the group consisting of 3, 5, 7, 9 and 11.

3. The allergy testing applicator according to claim 1, wherein said elongated handle has a first end and a second end defined along a longitudinal extent of said elongated handle, and one of said arms extends directly from a distal end of one of said first or second ends.

4. The allergy testing applicator according to claim 1, wherein:
said elongated handle has long sides and shorter sides both extending in a vertical direction;
a shoulder extending perpendicularly from both of said long sides of said elongated handle in a horizontal direction and away from said elongated handle, said shoulder extending over a majority of each of said long sides.

5. The allergy testing applicator according to claim 1, wherein said elongated handle has a bottom side and a shoulder extends out from said bottom side of said elongated handle.

6. The allergy testing applicator according to claim 1, wherein said upper tapered region is conical or parabolic in shape.

7. The allergy testing applicator according to claim 1, further comprising raised indicators, a respective one of said raised indicators is disposed on a top side of a respective one of said arms.

8. The allergy testing applicator according to claim 1, wherein said elongated handle has a plurality of ribs formed at a given angle to said elongated handle for assisting a hand of a user to grip said elongated handle.

9. The allergy testing applicator according to claim 1, further comprising reinforcements extending along a top of said arms.

* * * * *